(12) United States Patent
Stopek et al.

(10) Patent No.: US 8,932,621 B2
(45) Date of Patent: Jan. 13, 2015

(54) IMPLANTABLE FILM/MESH COMPOSITE

(71) Applicant: Covidien LP, Mansfield, MA (US)

(72) Inventors: Joshua Stopek, Guilford, CT (US);
Amin Elachchabi, Hamden, CT (US);
Daniel Broom, Branford, CT (US)

(73) Assignee: Covidien LP, Mansfield, MA (US)

( * ) Notice: Subject to any disclaimer, the term of this patent is extended or adjusted under 35 U.S.C. 154(b) by 20 days.

(21) Appl. No.: 13/650,237

(22) Filed: Oct. 12, 2012

(65) Prior Publication Data
US 2013/0102959 A1 Apr. 25, 2013

Related U.S. Application Data

(60) Provisional application No. 61/551,093, filed on Oct. 25, 2011.

(51) Int. Cl.
| | |
|---|---|
| A61B 17/08 | (2006.01) |
| A61F 2/00 | (2006.01) |
| A61F 2/02 | (2006.01) |
| A61L 31/00 | (2006.01) |
| A61L 31/04 | (2006.01) |
| A61L 31/06 | (2006.01) |
| A61L 31/14 | (2006.01) |
| A61L 31/16 | (2006.01) |

(52) U.S. Cl.
CPC .............. *A61F 2/0063* (2013.01); *A61L 31/005* (2013.01); *A61L 31/044* (2013.01); *A61L 31/048* (2013.01); *A61L 31/06* (2013.01); *A61L 31/148* (2013.01); *A61L 31/16* (2013.01)
USPC .......... 424/423; 606/151; 600/37; 623/23.72

(58) Field of Classification Search
USPC .......... 604/890.1, 891.1; 606/151; 623/23.72, 623/23.74; 602/41–59, 67–69, 76, 904; 600/29, 30, 37; 128/835, 848, 885; 206/440, 441; 424/423
See application file for complete search history.

(56) References Cited

U.S. PATENT DOCUMENTS

| | | | |
|---|---|---|---|
| 2,337,011 A * | 12/1943 | Young | 602/42 |
| 3,054,406 A | 9/1962 | Usher | |
| 3,887,699 A | 6/1975 | Yolles | |
| 4,767,628 A | 8/1988 | Hutchinson | |
| 4,931,546 A | 6/1990 | Tardy et al. | |
| 5,147,374 A | 9/1992 | Fernandez | |
| 5,195,542 A | 3/1993 | Gazielly et al. | |
| 5,254,133 A | 10/1993 | Seid | |

(Continued)

FOREIGN PATENT DOCUMENTS

| | | |
|---|---|---|
| EP | 1674048 A1 | 6/2006 |
| EP | 2 016 956 A2 | 1/2009 |

(Continued)

OTHER PUBLICATIONS

European Search Report for EP 12189673.2 date of completion is Jan. 29, 2013 (5 pages).

(Continued)

*Primary Examiner* — Theodore Stigell
*Assistant Examiner* — Benjamin Koo

(57) ABSTRACT

The present disclosure relates to implantable medical devices which include at least one mesh and at least one film attached to the mesh along different portions of the mesh creating at least one aperture between the mesh and the film.

20 Claims, 8 Drawing Sheets

(56) References Cited

U.S. PATENT DOCUMENTS

| | | |
|---|---|---|
| 5,258,000 A | 11/1993 | Gianturco |
| 5,368,602 A | 11/1994 | de la Torre |
| 5,370,650 A | 12/1994 | Tovey et al. |
| 5,593,441 A | 1/1997 | Lichtenstein et al. |
| 5,634,931 A | 6/1997 | Kugel |
| 5,695,525 A | 12/1997 | Mulhauser et al. |
| 5,702,416 A | 12/1997 | Kieturakis et al. |
| 5,711,960 A | 1/1998 | Shikinami |
| 5,743,917 A | 4/1998 | Saxon |
| 5,766,246 A | 6/1998 | Mulhauser et al. |
| 5,769,864 A | 6/1998 | Kugel |
| 5,916,225 A | 6/1999 | Kugel |
| 5,922,026 A | 7/1999 | Chin |
| 6,042,534 A | 3/2000 | Gellman et al. |
| 6,120,539 A | 9/2000 | Eldridge et al. |
| 6,162,962 A | 12/2000 | Hinsch et al. |
| 6,171,318 B1 | 1/2001 | Kugel et al. |
| 6,180,848 B1 | 1/2001 | Flament et al. |
| 6,210,439 B1 | 4/2001 | Firmin et al. |
| 6,214,020 B1 | 4/2001 | Mulhauser et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,270,792 B1 | 8/2001 | Guillemet et al. |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,319,264 B1 | 11/2001 | Törmälä et al. |
| 6,383,201 B1 | 5/2002 | Dong |
| 6,425,924 B1 | 7/2002 | Rousseau |
| 6,447,551 B1 | 9/2002 | Goldmann |
| 6,485,503 B2 | 11/2002 | Jacobs et al. |
| 6,500,777 B1 | 12/2002 | Wiseman et al. |
| 6,596,002 B2 | 7/2003 | Therin et al. |
| 6,610,006 B1 | 8/2003 | Amid et al. |
| 6,616,685 B2 | 9/2003 | Rousseau |
| 6,645,226 B1 | 11/2003 | Jacobs et al. |
| 6,669,735 B1 | 12/2003 | Pelissier |
| 6,712,859 B2 | 3/2004 | Rousseau et al. |
| 6,736,823 B2 | 5/2004 | Darois et al. |
| 6,736,854 B2 | 5/2004 | Vadurro et al. |
| 6,755,868 B2 | 6/2004 | Rousseau |
| 6,790,213 B2 | 9/2004 | Cherok et al. |
| 6,800,082 B2 | 10/2004 | Rousseau |
| 6,872,227 B2 | 3/2005 | Sump et al. |
| 6,926,723 B1 | 8/2005 | Mulhauser et al. |
| 7,011,688 B2 | 3/2006 | Gryska et al. |
| 7,021,086 B2 | 4/2006 | Ory et al. |
| 7,041,868 B2 | 5/2006 | Greene et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,101,381 B2 | 9/2006 | Ford et al. |
| 7,156,858 B2 | 1/2007 | Schuldt-Hempe et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,404,819 B1 | 7/2008 | Darios et al. |
| 7,556,598 B2 | 7/2009 | Rao |
| 7,594,921 B2 | 9/2009 | Browning |
| 7,785,334 B2 | 8/2010 | Ford et al. |
| 7,806,905 B2 | 10/2010 | Ford et al. |
| 8,123,817 B2 | 2/2012 | Intoccia et al. |
| 2002/0099344 A1 | 7/2002 | Hessel et al. |
| 2002/0131988 A1 | 9/2002 | Foster et al. |
| 2003/0130745 A1 | 7/2003 | Cherok et al. |
| 2003/0212460 A1 | 11/2003 | Darois et al. |
| 2004/0098118 A1 | 5/2004 | Granada et al. |
| 2004/0215219 A1 | 10/2004 | Eldridge et al. |
| 2004/0224007 A1 | 11/2004 | Zhang |
| 2005/0010078 A1* | 1/2005 | Jamiolkowski et al. ........ 600/30 |
| 2005/0240261 A1 | 10/2005 | Rakos et al. |
| 2005/0244455 A1 | 11/2005 | Greenawalt |
| 2005/0261782 A1 | 11/2005 | Hoganson |
| 2006/0034887 A1 | 2/2006 | Pelissier |
| 2006/0116696 A1 | 6/2006 | Odermatt et al. |
| 2006/0121078 A1 | 6/2006 | Trogolo et al. |
| 2006/0188546 A1 | 8/2006 | Giroux |
| 2006/0224038 A1 | 10/2006 | Rao |
| 2006/0253203 A1 | 11/2006 | Alvarado |
| 2007/0129736 A1 | 6/2007 | Solecki |
| 2007/0198040 A1 | 8/2007 | Buevich et al. |
| 2007/0244548 A1 | 10/2007 | Myers et al. |
| 2007/0260268 A1 | 11/2007 | Bartee et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0147200 A1 | 6/2008 | Rousseau et al. |
| 2008/0172071 A1 | 7/2008 | Barker |
| 2008/0199506 A1 | 8/2008 | Horres et al. |
| 2008/0255593 A1 | 10/2008 | St-Germain |
| 2009/0036996 A1 | 2/2009 | Roeber |
| 2009/0069826 A1 | 3/2009 | Walther et al. |
| 2009/0082792 A1 | 3/2009 | Koyfman et al. |
| 2009/0105526 A1 | 4/2009 | Piroli Torelli et al. |
| 2009/0125107 A1 | 5/2009 | Maxwell |
| 2009/0142385 A1 | 6/2009 | Gross et al. |
| 2009/0163936 A1 | 6/2009 | Yang et al. |
| 2009/0171377 A1 | 7/2009 | Intoccia et al. |
| 2009/0187197 A1 | 7/2009 | Roeber et al. |
| 2009/0192530 A1 | 7/2009 | Adzich et al. |
| 2009/0198260 A1 | 8/2009 | Ford et al. |
| 2009/0270999 A1 | 10/2009 | Brown |
| 2009/0276057 A1 | 11/2009 | Trabucco et al. |
| 2009/0326676 A1 | 12/2009 | Dupic et al. |
| 2010/0003308 A1 | 1/2010 | Tapolsky et al. |
| 2010/0089409 A1 | 4/2010 | Bertagnoli |
| 2010/0160375 A1 | 6/2010 | King |
| 2010/0286716 A1 | 11/2010 | Ford et al. |
| 2010/0292717 A1 | 11/2010 | Petter et al. |
| 2011/0144667 A1 | 6/2011 | Horton et al. |
| 2011/0238094 A1* | 9/2011 | Thomas et al. ............... 606/151 |
| 2011/0265283 A1 | 11/2011 | Duncan |
| 2012/0082712 A1* | 4/2012 | Stopek et al. ............ 424/423 |
| 2012/0329901 A1* | 12/2012 | Belcheva et al. ............ 522/111 |
| 2013/0138124 A1* | 5/2013 | Criscuolo et al. ............ 606/151 |

FOREIGN PATENT DOCUMENTS

| | | |
|---|---|---|
| EP | 2 404 571 A1 | 1/2012 |
| FR | 2 601 371 A1 | 1/1988 |
| FR | 2 857 851 A1 | 1/2005 |
| WO | WO 93/11805 A1 | 6/1993 |
| WO | WO 99/51163 A1 | 10/1999 |
| WO | WO 02/34304 A1 | 5/2002 |
| WO | WO 03/007847 A1 | 1/2003 |
| WO | WO 2006/020922 A2 | 2/2006 |
| WO | WO 2006/036967 A1 | 4/2006 |
| WO | WO 2006/102374 A2 | 9/2006 |
| WO | WO 2008/127411 A1 | 10/2008 |
| WO | WO 2009/075786 A1 | 6/2009 |
| WO | WO 2010/093333 A1 | 8/2010 |
| WO | WO 2011/038740 A1 | 4/2011 |

OTHER PUBLICATIONS

European Search Report corresponding to European Application No. 11185681.1-1219; date of completion is Aug. 13, 2012 (8 pages).
European Search Report corresponding to European Application No. 11250362.8-1257; date of completion is Jul. 29, 2011 (3 Pages).
European Search Report corresponding to European Application No. 11250361.0-1257; date of completion is Jul. 25, 2011 (3 Pages).
European Search Report corresponding to European Application No. 11250363.6-1257; date of completion is Jul. 28, 2011 (3 Pages).
European Search Report corresponding to European Application No. 11250641.5-2320 (3 Pages).
Cohen, et al., Dis Colon Rectum, Jun. 2005; 48(6); 1130-9.

* cited by examiner

IMPLANTABLE FILM/MESH COMPOSITE

CROSS-REFERENCE TO RELATED APPLICATIONS

This application claims the benefit of and priority to U.S. Provisional Patent Application No. 61/551,093, filed Oct. 25, 2011, the entire disclosure of which is incorporated by reference herein.

BACKGROUND

1. Technical Field

The present disclosure relates generally to implantable medical devices, and more particularly, to implantable medical devices which include at least one mesh attached to at least one film, wherein the film has at least a first and second portion attached to different portions of the mesh and third film portion positioned therebetween which is unattached to the mesh.

2. Background of Related Art

Surgical meshes may be used during both laparoscopic and open surgery for repair of many types of defects and injuries. For example, surgical meshes are commonly used in the repair of hernias. The meshes may be used to provide support to surrounding tissue.

During hernia repair, a mesh may be placed over the entirety of damaged tissue and some of the healthy tissue surrounding the defect. The mesh can be held in place by a fixation device that attaches the mesh to the surrounding tissue. A variety of different fixation devices may be used to anchor the mesh into the tissue. The mesh may further include an additional layer such as a film, for sustained delivery of analgesic agents to the vicinity of the mesh implant for reduction of acute post-operative pain. Integration of films to accommodate unique patient/anatomical features while maintaining the integrity of the film/mesh attachment is desired.

SUMMARY

Accordingly, the present disclosure relates to implantable medical devices which include a surgical mesh and a film having at least first and second portions attached to the mesh and a third portion positioned between therebetween and unattached to the mesh creating an aperture therebetween. The mesh may generally be a textile or fabric created to promote tissue ingrowth and support injured tissue. The film may generally be polymeric in nature and may be intended to further enhance the ingrowth of tissue into the implant, prevent adhesions of surrounding tissue, deliver therapeutic agents and/or simply provide addition support to the implant. In certain embodiments, the implantable medical device further includes at least one therapeutic agent. In some embodiments, the implant may include a plurality of: film portions attached to the mesh; film portions unattached to the mesh; and/or apertures.

In some embodiments, the implantable medical device may include a first mesh having a first outer edge and a first inner edge, a second mesh having a second outer edge and a second inner edge, and, a film having at least a first portion attached to the first outer edge of the first mesh and at least a second portion attached to the outer edge of the second mesh, wherein the first and second inner edges are reversibly attached.

In other embodiments, the implantable medical device may include a mesh, a first film having a first film portion attached to a first mesh portion of the mesh and a second film portion unattached to the mesh, and, a second film having a second film portion attached to a second mesh portion of the mesh and a second film portion unattached to the mesh, wherein the second film portion overlaps the first film portion.

Methods of forming and implanting such devices are also disclosed.

BRIEF DESCRIPTION OF THE DRAWINGS

The foregoing objects and advantages of the disclosure will become more apparent from the reading of the following description in connection with the accompanying drawings, in which.

DETAILED DESCRIPTION

Figure 1A:
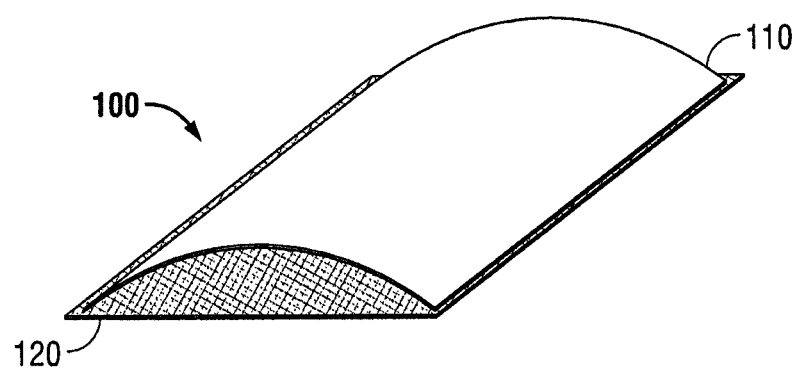
FIGS. 1A and 1B are a perspective view and side view, respectively, of an implantable medical device according to one embodiment described in the present disclosure.

The present disclosure relates to implantable medical devices which include a surgical mesh connected to a film with an aperture positioned between the mesh and a portion of the film. The film includes a first and second portion which is attached to a first and second portion of the mesh. The film further includes a third or free portion which is positioned between the first and second film portions which is unattached to and spaced a distance from any portion of the mesh, creating an aperture between the film and the mesh. In certain embodiments, the implantable medical device further includes at least one therapeutic agent.

By implantable, the medical devices described herein may be positioned for any duration of time at a location within a body, such as within a portion of the abdominal cavity. Furthermore, the terms "implantation" and "implanted" refer to the positioning, for any duration of time, of a medical device at a location within a body, such as within a portion of the abdominal cavity.

The implantable medical devices described herein include at least one surgical mesh. The surgical mesh described herein may include porous fabrics made from intertwined filaments. The filaments may extend horizontally and vertically in a manner which produces sections where the filaments crossover one another creating points of common intersection. The surgical mesh may be woven, non-woven, knitted or braided. In some embodiments, the filaments may form two-dimensional or three-dimensional meshes. Some examples of two-dimensional and/or three-dimensional mesh substrates may be found in U.S. Pat. No. 7,021,086, U.S. Pat. No. 6,596,002, U.S. Pat. No. 7,331,199, the entire contents of which are incorporated by reference herein.

Suitable meshes for use in the present disclosure include, for example, a collagen composite mesh such as PARIETEX™ Composite Mesh (commercially available from Tyco Healthcare Group LP, d/b/a Covidien). PARIETEX™ Composite Mesh is a 3-dimensional polyester weave with a resorbable collagen film bonded on one side. Another suitable mesh includes Parietex Progrip™ self-fixating mesh (also commercially available from Covidien). Parietex Progrip™ is a polyester mesh which includes poly lactic acid (PLA) grip members. Other suitable meshes include those sold under the names PARIETENE®, PARIETEX™, SURGIPRO™ (all commercially available from Covidien); PROLENE™ (commercially available from Ethicon, Inc.); MARLEX®, DULEX®, 3D MAX® mesh, PERFIX® plug, VENTRALEX®, and KUGEL® patch (all commercially available from C.R. Bard, Inc.); PROLITE™, PROLITE ULTRA™ (all commercially available from Atrium Medical); COMPOSIX®, SEPRAMESH®, and VISILEX® (all commercially available from Davol, Inc.); and DUALMESH®, MYCROMESH®, and INFINIT® mesh (all commercially available from W.L. Gore). In certain preferred embodiments, Parietex™ Composite Mesh or Parietex™ Pro-grip may be utilized in accordance with the present invention.

Additionally, meshes within the scope and context of this disclosure may include biologic materials such as allografts (i.e., AlloDerm® Regenerative Tissue Matrix from Lifecell), autografts, and xenografts (i.e., PERMACOL™, from Covidien). In alternate embodiments, processed/purified tissues may also be employed. It should be noted that allografts, xenografts, and autografts may not comprise intertwined filaments, but rather may comprise a scaffold or film construction.

Certain meshes within the scope of the present disclosure may comprise monofilaments or multi-filaments. In certain embodiments, a plurality of multi-filaments may be combined to form yarns. In other embodiments, a core-sheath construction may be employed. It is envisioned that the mesh may be configured to any size and/or shape suitable for hernia repair.

In certain embodiments, such as Parietex™ Composite Mesh or Parietex™ Pro-grip, the mesh may be knit on a warp knitting machine, of the tricot or Raschel type, with at least three sheets or warps of yarn and as many guide bars.

Figure 10:
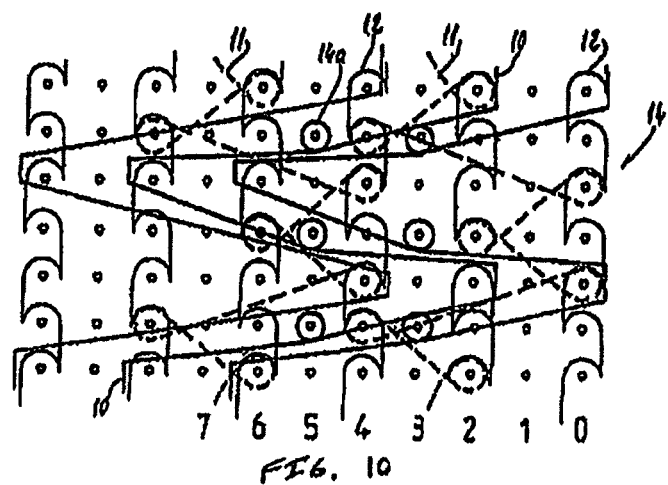
FIG. 10 is a diagram showing the weave of three sheets forming a medical device according to one embodiment described in the present disclosure.

In more detail, a rear bar is threaded, one guide full and one guide empty, with first mono- or multi-filaments 10 of a biocompatible polymer as represented as a solid line in FIG. 10. An intermediate bar is threaded, one guide full, three guides empty, with second mono- or multi-filaments 11 of a biocompatible polymer as represented as a broken line in FIG. 10. The intermediate bar works in such a way as to obtain a zigzag openwork pattern between the columns of meshes. Finally, a front bar is threaded, one guide full, one guide empty, and works in a chain stitch with third mono- or multi-filaments 12 a biocompatible polymer as represented by a thin line in FIG. 10. The third filament 12, i.e., a chain stitch, imprisons first filament 10 and maintains the length of the mesh while contributing to the formation of the mesh with the intermediate sheet formed by the second filament 11. The different filaments may form yarns and may be worked according to the following chart:

| Raschel | Warp | | |
| --- | --- | --- | --- |
| | Rear bar I<br>Front bar I | Intermediate bar II<br>Intermediate bar II | Front bar III<br>Rear bar III |
| | 7 | 3 | 1 |
| | 7 | 2 | 0 |
| | — | — | — |
| | 3 | 4 | 0 |
| | 4 | 5 | 1 |
| | — | — | — |
| | 0 | 1 | |
| | 0 | 0 | |
| | — | — | |
| | 4 | 2 | |
| | 3 | 3 | |
| | | — | |
| | | 1 | |
| | | 0 | |
| | | — | |
| | | 4 | |
| | | 5 | |

The rear bar places the first filament or yarn in partial weft under the chain stitch and "thrown" onto the needle not forming a chain stitch. For this reason, at the next row, the needle not forming a chain stitch not being supplied permits escape of the filament which forms a loop 14a projecting from the front face of the mesh.

The threading—one guide full, three guides empty—in the intermediate bar, associated with the displacement, makes it possible to form a light ground texture, stable in width, and open-worked to permit good tissue integration.

The mesh 14 thus obtained may be provided with loops 14a (FIG. 11) which may be perpendicular to one of the mesh surfaces. Loops 14a may also include a rigidity and hold at a right angle which may be obtained by the rigidity or nerve of the filaments employed. This rigidity may be necessary for the subsequent formation of grip members which ensure a grip function to at least a portion of the implantable medical device.

Figure 11:
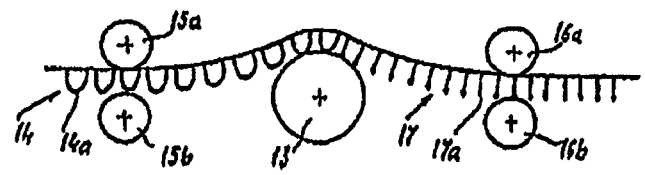
FIG. 11 is a diagrammatic side view of a device permitting the formation of spiked naps on the medical device of FIG. 9 according to another embodiment described in the present disclosure.

On leaving the loom, mesh 14 may be subjected to a thermosetting operation which stabilizes the mesh length and width. The mesh may then be subjected to a phase of formation of the grip members consisting, as is shown in FIG. 11, in passing the mesh over a cylinder 13 containing an electrical heating resistor. Mesh 14 is pressed flat on cylinder 13 by two pairs of rollers, upstream 15a, 15b and downstream 16a, 16b, respectively, which are vertically displaceable for controlling this pressing force.

This control as well as that of the temperature of the resistor placed in cylinder 13 and of the speed of movement of mesh 14 across cylinder 13 make it possible to melt the head of each of loops 14a so that each loop 14a forms two grip members 17.

Each grip member 17 thus may have a substantially rectilinear body protruding perpendicularly with respect to mesh 14 and, at the free end of this body, a head 17a of greater width than that of the body. Head 17a has a generally spheroidal shape or a mushroom shape. Grip member 17 gives mesh 14 the ability to attach to tissue when implanted. In addition, grip members 17 may attach to other portions of mesh 14 when folded, rolled or manipulated in any other way. The grip members may be positioned along any portion of the mesh and in any quantity and/or configuration. For example, in some embodiments, the grip members may be positioned on the same portion of the mesh as the film. In other embodiments, the grip members may be positioned on a different portion of the mesh which does not include the film.

Alternatively, the mesh may be formed using other methods such as those within the purview of one skilled in the art, including, but not limited to weaving, knitting, braiding, crocheting, extruding, spraying, casting, molding, and combinations thereof. Meshes formed therefrom may comprise two or three dimensional constructs.

The implantable devices described herein may be made from non-bioabsorbable materials, such as polypropylene, polyethylene, polyethylene terephthalate, polytetrafluoroethylene, and the like. In one specific embodiment, the mesh may comprise polypropylene or polyethylene terephthalate.

Alternatively, or in addition to, the implantable devices may comprise bioabsorbable materials. Some non-limiting examples include polysaccharides such as cellulose, dextran, chitin, chitosan, alginate, pectin, mucilage, pullalan, methylcellulose, carboxymethylcellose, hydroxypropyl methylcellulose, hyaluronic acid (HA), hydroxyethyl methylcellulose, arabinoxylans, bacterial polysaccharides and combinations thereof. In certain embodiments, the film layer may comprise carboxymethylcellulose.

Some additional non-limiting examples of bioabsorbable materials used to form the implantable devices include polymers selected from the group consisting of aliphatic polyesters; polyamides; polyamines; polyalkylene oxalates; poly (anhydrides); polyamidoesters; copoly(ether-esters); poly (carbonates) including tyrosine derived carbonates; poly (hydroxyalkanoates) such as poly(hydroxybutyric acid), poly (hydroxyvaleric acid), and poly(hydroxybutyrate); polyimide carbonates; poly(imino carbonates) such as such as poly (bisphenol A-iminocarbonate and the like); polyorthoesters; polyoxaesters including those containing amine groups; polyphosphazenes; poly (propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

More specifically, aliphatic polyesters include, but are not limited to, homopolymers and copolymers of lactide (including lactic acid, D-, L- and meso lactide); glycolide (including glycolic acid); epsilon-caprolactone, p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof. In one particular embodiment, the film may comprise at least one aliphatic polyester.

Other suitable bioabsorbable materials which may be used in the implantable device include but are not limited to poly (amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; mucilage, pectin; and combinations thereof.

The term "collagen" is meant to include any type of collagen, whether natural or synthetic, of human or animal origin, such as, for example, enriched human collagen of type I, human collagen of type III, also enriched, human collagen of type I+III or of type IV or other collagens such as animal collagen of type I or of type I+III. The collagen may be oxidized or non-oxidized.

In certain embodiments, the collagen may be oxidized without crosslinking. For example, native collagen may be dipped in an acid solution and/or washed, to eliminate the telopeptides, notably by pepsin digestion.

The collagen may also be modified by oxidative cleavage. For this purpose periodic acid or one of its salts can be used, applying the technique described by M. TARDY et al. (FR-A-2 601 371 and U.S. Pat. No. 4,931,546, the entire contents of which are herby incorporated by reference).

It is recalled briefly that this technique consists of mixing the collagen in acid solution with a solution of periodic acid or one of its salts at a concentration of between 1 and $10^{-5}$M, preferably between $5 \cdot 10^{-3}$ and $10^{-1}$ M, at a temperature of between 10 and 25° C. for 10 minutes to 72 hours.

This process breaks down some of the collagen's components, these being hydroxylysine and the sugars, thus creating reactive sites without causing crosslinking.

The oxidative cleavage of collagen allows moderate cross-linking later in the collagenic material but does not exclude the possibility of providing this function by other means of moderate cross-linking, for example by beta or gamma irradiation, or other agents of moderate cross-linking, for example chemical reagents at suitably low and non-toxic doses.

For some applications, the polymer film layers described herein may include collagen which is not oxidized or a mixture in any proportions of non-oxidized and oxidized collagens.

Additionally, synthetically modified natural polymers such as cellulose and polysaccharide derivatives, including alkyl celluloses, hydroxyalkyl celluloses, cellulose ethers, cellulose esters, nitrocelluloses, and chitosan may be utilized. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses."

Both the mesh and/or the film may further consist of at least one optional ingredient. Some examples of suitable optional ingredients include emulsifiers, viscosity enhancers, dyes, pigments, fragrances, pH modifiers, wetting agents, plasticizers, antioxidants, and the like. The optional ingredients may represent up to about 10% of the implantable medical device by weight.

In some embodiments, the film may include at least one plasticizer, i.e., glycerol, PEG, etc. For instance, in some embodiments, the film may include a combination of carboxymethylcellulose and glycerol. In other embodiments, the film may include collagen, and at least one of PEG and glycerol.

Alternatively, the film may comprise a copolymer of glycolide and caprolactone. More particularly, the film may contain a copolymer of about 10% glycolide and about 90% caprolactone.

In yet alternate embodiments, the film may comprise a copolymer of glycolide, trimethylene carbonate, caprolactone and lactide. More particularly, the film may contain about 69% glycolide, about 7% trimethylene carbonate, about 17% caprolactone and about 7% lactide.

In yet other embodiments, the film may comprise a copolymer of glycolide, dioxanone, and trimethylene carbonate. More particularly, the film may contain a copolymer of about 60% glycolide, about 14% dioxanone, and about 26% trimethylene carbonate.

The films described herein may be formed by any suitable method known to those skilled in the art. In certain embodiments, a solution may be formed which includes the suitable polymeric material and any optional ingredients. Polymers solutions described herein include suspensions, emulsions, dispersions and the like. The polymer may represent from about 1.0% to about 50% (w/w) in the solution. The solution may be cast bulk sheet stock, spray coated using an ultrasonic sprayer, extruded, molded and the like, to form the films described herein.

Suitable solvents which may be in polymer solutions include, without limitation, methylene chloride, chloroform, N-methylpyrrolidone, tetrahydrofuran, dimethylformamide, methanol, ethanol, hexanes, acetone and combinations thereof.

In some embodiments, the polymer solution may be cast into a film directly on a portion of the mesh surface. In other embodiments, the film may be spray coated directly on a portion of the mesh. In still other embodiments, the film may be formed before being connected to the mesh.

In certain embodiments, the film may be created using a spraying technique, such as ultrasonic spraying. Spraying films results in a unique ability to include a high therapeutic payload of a therapeutic agent. For example, the medical device as described herein may be fabricated by passing a first solution containing a hydrophobic polymer and a second solution containing a therapeutic agent through an ultrasonic spray nozzle to form droplets. The droplets may be mixed while falling towards or being deposited onto an inert substrate, such as silicone sheet, or a portion of the mesh to form a film. In some embodiments, prior to spraying the film, an inert substrate may be positioned on the portion of the mesh which the film is not meant to become fixedly attached to. Thus, upon formation of the film, the film may adhere to the portions of the mesh which are not covered by the inert substrate and the film will not fixedly attach to the portions of the mesh which are covered by the inert substrate. In yet another embodiment, the polymeric film layer may be formed using an ultrasonic spraying nozzle onto an inert substrate.

In some embodiments, the films include a single layer containing a hydrophobic polymer and a therapeutic agent. In other embodiments, the films include a first layer containing a hydrophobic polymer and a second layer containing a therapeutic agent. In still other embodiments, the films include a tri-layer structure wherein a second layer containing a therapeutic agent is positioned between a first layer containing a hydrophobic polymer and a third layer containing the same or different hydrophobic polymer.

In certain embodiments, the hydrophobic polymers of the films may include aliphatic polyesters such as include lactide, glycolide, dioxanone, trimethylene carbonate, and ε-caprolactone. For example, the therapeutic agents described herein may be combined with copolymers, i.e., random, or block copolymers, of lactide and glycolide or glycolide and ε-caprolactone. Increasing the amount of glycolide may increase the films degradation rate. While increasing the amount of lactide and/or caprolactone may extend the degradation/absorption profile of the film. For example, lactide rich copolymers, i.e., greater than about 50% lactide, may be particularly useful to enhance a particular polymer's solubility, such as glycolide.

Suitable therapeutic agents and drugs may be incorporated into the implantable medical devices described herein. The term "therapeutic agent", as used herein, is used in its broadest sense and includes any substance or mixture of substances that provides a beneficial, therapeutic, pharmacological, and/or prophylactic effect. The agent may be a drug which provides a pharmacological effect.

The term "drug" is meant to include any agent capable of rendering a therapeutic effect, such as, anti-adhesives, antimicrobials, analgesics, antipyretics, anesthetics (e.g. local and systemic), antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes. It is also intended that combinations of agents may be used.

Other therapeutic agents, which may be included as a drug include: anti-fertility agents; parasympathomimetic agents; psychotherapeutic agents; tranquilizers; decongestants; sedative hypnotics; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; antiinflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; and immunological agents.

Other examples of suitable agents, which may be included in the films described herein include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (e.g., IL-2, IL-3, IL-4, IL-6); interferons (e.g., β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids such as antisense molecules, DNA, RNA, and RNAi; oligonucleotides; polynucleotides; and ribozymes.

Some specific non-limiting examples of water-soluble drugs that may be used in the present polymeric films include, lidocaine, bupivacaine, capsaicin, tetracaine, procaine, dibucaine, sirolimus, taxol, chlorhexidine, polyhexamethylene, thiamylal sodium, thiopental sodium, ketamine, flurazepam, amobarbital sodium, phenobarbital, bromovalerylurea, chloral hydrate, phenyloin, ethotoin, trimethadione, primidone, ethosuximide, carbamazepine, valproate, acetaminophen, phenacetin, aspirin, sodium salicylate, aminopyrine, antipyrine, sulpyrine, mepirizole, tiaramide, perixazole, diclofenac, anfenac, buprenorphine, butorphanol, eptazocine, dimenhydrinate, difenidol, dl-isoprenaline, chlorpromazine, levomepromazine, thioridazine, fluphenazine, thiothixene, flupenthixol, floropipamide, moperone, carpipramine, clocapramine, imipramine, desipramine, maprotiline, chlordiazepoxide, clorazepate, meprobamate, hydroxyzine, saflazine, ethyl aminobenzoate, chlorphenesin carbamate, methocarbamol, acetylcholine, neostigmine, atropine, scopolamine, papaverine, biperiden, trihexyphenidyl, amantadine, piroheptine, profenamine, levodopa, mazaticol, diphenhydramine, carbinoxamine, chlorpheniramine, clemastine, aminophylline, choline, theophylline, caffeine, sodium benzoate, isoproterenol, dopamine, dobutamine, propranolol, alprenolol, bupranolol, timolol, metoprolol, procainamide, quinidine, ajmaline, verapamil, aprindine, hydrochlorothiazide, acetazolamide, isosorbide, ethacrynic acid, captopril, enalapril, delapril, alacepril, hydralazine, hexamethonium, clonidine, bunitrolol, guanethidine, bethanidine, phenylephrine, methoxamine, diltiazem, nicorandil, nicametate, nicotinic-alcohol tartrate, tolazoline, nicardipine, ifenprodil, piperidinocarbamate, cinepazide, thiapride, dimorpholamine, levallorphan, naloxone, hydrocortisone, dexamethasone, prednisolone, norethisterone, clomiphene, tetracycline, methyl salicylate, isothipendyl, crotamiton, salicylic acid, nystatin, econazole, cloconazole, vitamin $B_1$, cyclothiamine, vitamin $B_2$, vitamin $B_3$, vitamin $B_5$, vitamin $B_6$, vitamin $B_7$, vitamin $B_9$, vitamin $B_{12}$, vitamin C, nicotinic acid, folic acid, nicotinamide, calcium pantothenate, pantothenol, panthetin, biotin, ascorbic acid, tranexamic acid, ethamsylate, protamine, colchicine, allopurinol, tolazamide, glymidine, glybuzole, metoformin, buformin, orotic acid, azathioprine, lactulose, nitrogen mustard, cyclophophamide, thio-TEPA, nimustine, thioinosine, fluorouracil, tegafur, vinblastine, vincristine, vindesine, mitomycin C, daunorubicin, aclarubicin, procarbazine, cisplatin, methotrexate, benzylpenicillin, amoxicillin, penicillin, oxycillin, methicillin, carbenicillin, ampicillin, cefalexin, cefazolin, erythromycin, kitasamycin, chloramphenicol, thiamphenicol, minocycline, lincomycin, clindamycin, streptomycin, kanamycin, fradiomycin, gentamycin, spectinomycin, neomycin, vanomycin, tetracycline, ciprofloxacin, sulfanilic acid, cycloserine, sulfisomidine, isoniazid, ethambutol, acyclovir, gancyclovir, vidabarine, azidothymidine, dideoxyinosine, dideoxycytosine, morphine, codeine, oxycodone, hydrocodone, cocaine, pethidine, fentanyl, polymeric forms of any of the above drugs and any combinations thereof. Further, water-soluble drugs may not need be converted to a salt form, i.e., tetracycline hydrochloride, or bupivacaine hydrochloride. In some embodiments, the therapeutic agent may include an anesthetic, i.e., bupivacaine, bupivacaine hydrochloride, lidocaine, benzocaine, and the like.

Although the above therapeutic agents have been provided for the purposes of illustration, it should be understood that the present disclosure is not so limited. In particular, although certain therapeutic agents are specifically referred to above, the present disclosure should be understood to include analogues, derivatives and conjugates of such agents.

The therapeutic agent may be combined with any portion of the medical device, including the mesh and/or the film. In some embodiments, the therapeutic agent may be included in the polymeric film to provide sustained release of the therapeutic agent following implantation. Because the film may include a high payload of therapeutic agent, the polymeric films may provide sustained release of the agent for longer periods of time.

Figure 1B:
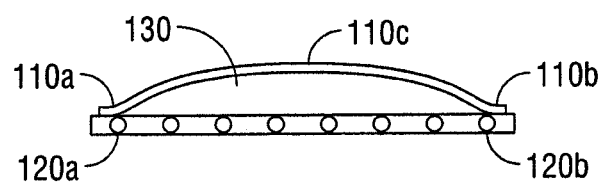

Turning now to FIGS. 1A and 1B, implantable medical device 100 is illustrated including film 110 at least partially attached to mesh 120. First and second film portions 110a and 110b are shown attached to first and second mesh portions 120a and 120b, respectively. Third film portion 110c is positioned between first and second film portions 110a, 110b and third film portion 110c is unattached and/or free of any portion of mesh 120 thereby creating aperture 130 between third film portion 110c and mesh 120. The third portion 110c is spaced a distance from the mesh and the spacing distance may vary depending on application. It is envisioned that tubular tissues, such as the esophagus, intestines, blood vessels, and/or non-tubular tissues, such as the spermatic chord, ligaments, tendons and the like may be positioned within the aperture between the film and the mesh.

Figure 2A:
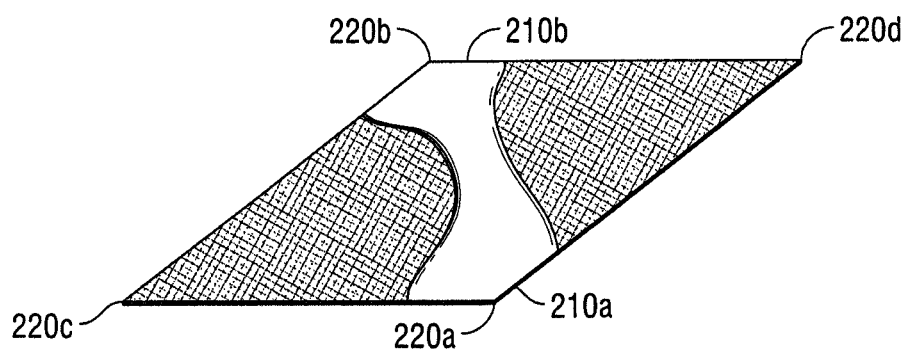
FIGS. 2A and 2B are a perspective view and side view, respectively, of an implantable medical device according to another embodiment described in the present disclosure.
Figure 2B:
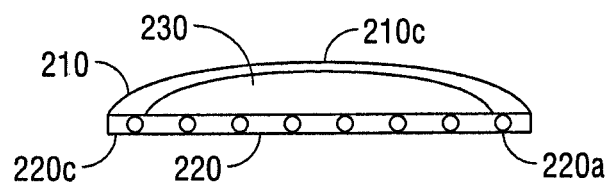

In FIGS. 2-4, the implantable medical devices are illustrated including a film which extends from at least a first corner to a second corner of the mesh. For instance, in FIGS. 2A-2B, film 210 includes first film portion 210a attached to first mesh corner 220a and second film portion 210b attached to second mesh corner 220b. Third film portion 210c extends between first and second film portions 210a, 210b, respectively, and is unattached to/free from and in certain embodiments, spaced a distance from of any portion of mesh 220 thereby creating aperture 230 between third film portion 210c and mesh 220 and extending diagonally from first mesh corner 220a to second mesh corner 220b. In such an embodiment, third and fourth mesh corners 220c and 220d are shown free of any film.

Figure 3A:
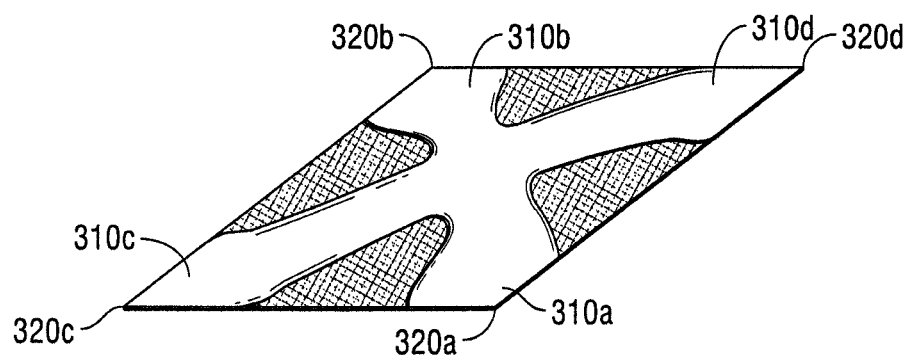
FIGS. 3A and 3B are a perspective view and side view, respectively, of an implantable medical device according to yet another embodiment described in the present disclosure.
Figure 3B:
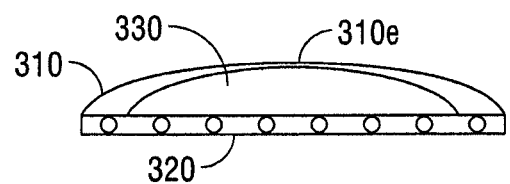

In FIGS. 3A-3B, film 310 includes a plurality of film portions 310a-d attached to a plurality of corners 320a-d of mesh 320 with a central film portion 310e positioned centrally between the plurality of film portions 310a-d and unattached of any portion of mesh 320 thereby creating aperture 330.

Figure 4A:
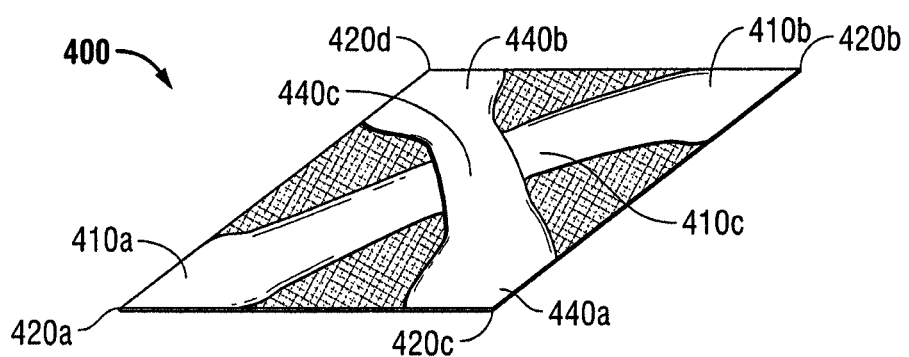
FIGS. 4A and 4B are a perspective view and side view, respectively, of an implantable medical device according to still another embodiment described in the present disclosure.
Figure 4B:
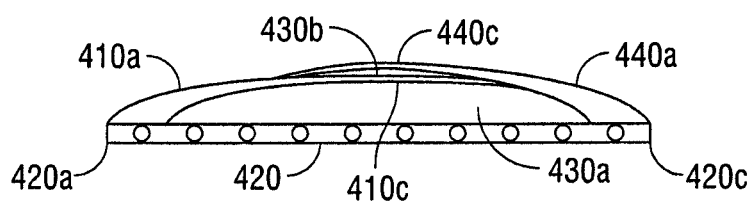

In still another embodiment as depicted in FIGS. 4A-4B, implantable medical device 400 includes first and second film 410 and 440, respectively, partially attached to mesh 420. First and second portions 410a and 410b, respectively, of first film 410 are attached to first and second mesh corners 420a and 420b, respectively. Third portion 410c of first film 410 extends between first and second portions 410a and 410b and is unattached and/or free of any portion of mesh 420 thereby creating first aperture 430a between first film 410 and mesh 420 and extending diagonally from first mesh corner 420a to second mesh corner 420b. In addition, first and second portions 440a and 440b, respectively, of second film 440 are attached to third and fourth mesh corners 420c and 420d, respectively. Third portion 440c of second film 440 extends between first and second portions 440a and 440b of second film 440 and is unattached and/or free of any portion of mesh 420 and first film 410 thereby creating second aperture 430b between second film 440 and first film 410 and/or mesh 420 and extending diagonally from third mesh corner 420c to fourth mesh corner 420d. In such an embodiment, the plurality of films and/or apertures may be useful in creating an implant capable of supporting tissue in multiple planes and/or directions. For examples, a first tissue type may be positioned within first aperture 430a while a second tissue type may be positioned within second aperture 430b with third portion 410c of first film 410 positioned therebetween.

Figure 5:
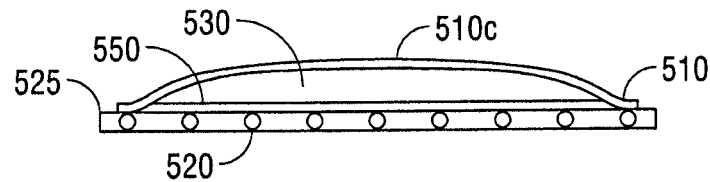
FIG. 5 is a side view of an implantable medical device according to one embodiment described in the present disclosure.
Figure 6:
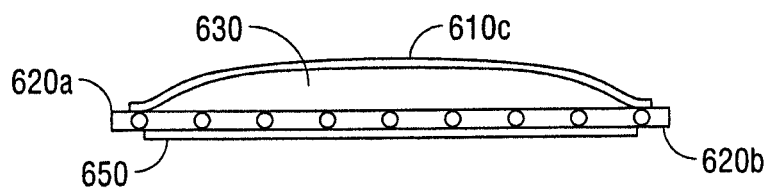
FIG. 6 is a side view of an implantable medical device according to another embodiment described in the present disclosure.

Although the devices previously described herein include a film portion which is free of the mesh, in some embodiments, the devices may further include an additional film layer positioned along the surface of the mesh. As illustrated in FIGS. 5 and 6, this additional film layer may be positioned along any surface of the mesh. For instance, as shown in FIG. 5, second film layer 550 may be positioned along surface 525 of mesh 520 between third film portion 510c and mesh 520. In such an embodiment, aperture 530 may be at least partially encased by film materials which are supported on at least one side by mesh 520. This type of implant may deliver a therapeutic agent to all sides of the tissue surrounded by the film materials when the therapeutic agent is included in the film materials. In other embodiments, the additional second film layer may alternatively, or in combination with, be positioned on a surface of the mesh opposite the aperture as depicted in FIG. 6, wherein aperture 630 is shown on a first surface 620a of mesh 620 and additional surface film layer 650 is shown on a second surface 620b of mesh 620 opposite first surface 620a.

Figure 7A:
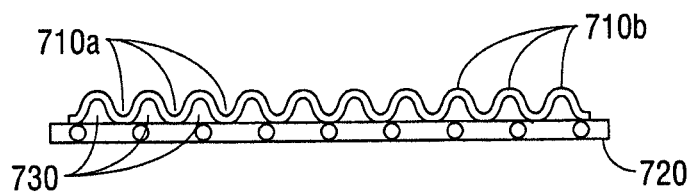
FIGS. 7A and 7B are side views of an implantable medical device according to yet another embodiment described in the present disclosure.
Figure 7B:
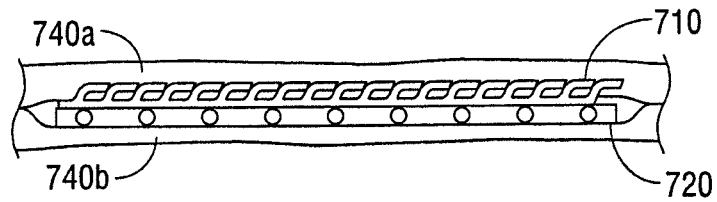

In still other embodiments, the implantable medical devices described herein may include a plurality of apertures positioned between the film layer and the mesh. For example, as shown in FIGS. 7A and 7B, film 710 includes a plurality of attached film portions 710a attached to mesh 720 and a plurality of unattached film portions 710b unattached and/or free of mesh 720 with a plurality of apertures 730 positioned therebetween. The unattached film portion 710b may be spaced a distance from mesh 720. The unattached film portions 710b may be spaced varying distances from the mesh to accommodate different sized and dimensioned organs. Additionally, it is envisioned that such a design may increase the surface area of film 710 along a given area of mesh 720 to interact with tissue when implanted. It is further envisioned that the increase in surface interaction between the film and the tissue may be useful in delivering higher payloads of a therapeutic agent without increasing the surface area of the delivery device. For example, as shown in FIG. 7B, upon implantation, the tissue may apply pressure to the implant and causing film 710 to flatten. In embodiments wherein the film includes a therapeutic agent, such a design allows for the delivery of an increased amount of the agent without adding the additional biocompatible material of the mesh device, which may often be made of a non-absorbable and potentially inflammatory-inducing material.

Figure 8A:
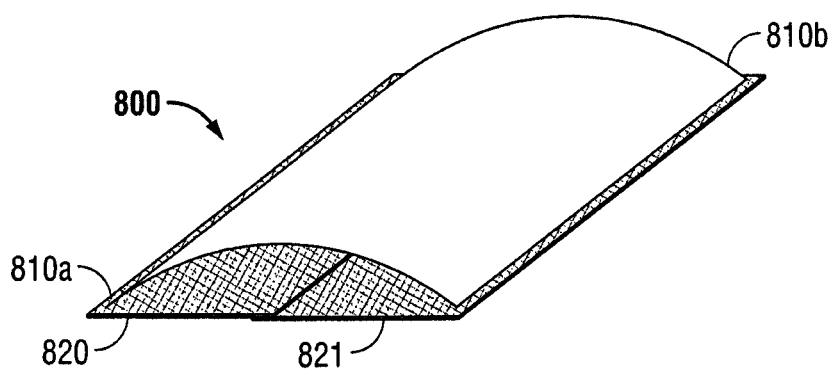
FIG. 8A is a perspective view of an implantable medical device according to still another embodiment described in the present disclosure.
Figure 8B:
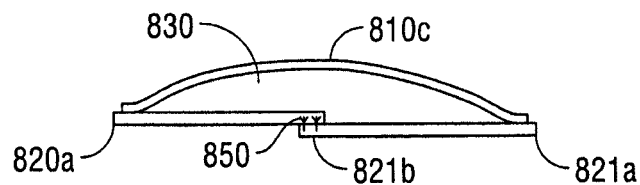
FIGS. 8B and 8C are side views of the implantable medical device shown in FIG. 8A.
Figure 8C:
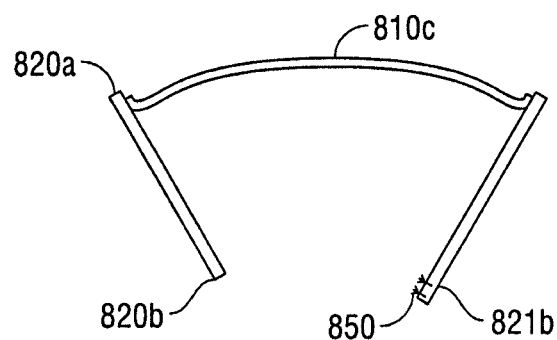

In yet other embodiments, the medical devices described herein may further include at least one layer which is capable of being separated to allow for a tissue to be passed therethrough and be positioned within the aperture. For example, as shown in FIGS. 8A-8C, implant 800 includes a film 810 attached to a first mesh 820 and a second mesh 821. The film 810 has a first portion 810a attached to a first outer edge of the first mesh 820 and a second portion 810b attached to a second outer edge of the second mesh 821. The first and second meshes 820 and 821 are removably affixed or connected to one another. First and second mesh 820 and 821 each include an outer edge or 820a and 821a and an inner edge 820b and 821b, wherein the inner edges 820b and 821b of the first and second mesh overlap. The inner edge portions of the first and second mesh may be removably or reversibly attached via a connector, such as an adhesive, suture, clip, grip-member and/or barb. As shown in FIGS. 8B and 8C, a plurality of grip-members 850 are positioned along inner edge 821b of second mesh 821 to removably attach the two mesh portions together. It is envisioned that such a mesh may be peeled apart to create an opening for the passage of tissue and then reattached with the tissue positioned within the aperture of the implant between the film and the mesh. It is further envisioned that the connector, i.e., grip-member or barb, may be positioned on either or both of the first and second mesh.

Figure 9A:
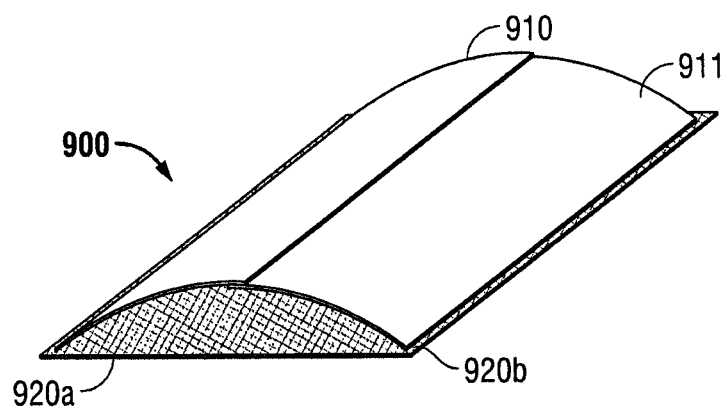
FIGS. 9A and 9B are a perspective view and a side view, respectively, of an implantable medical device according to yet another embodiment described in the present disclosure.
Figure 9B:
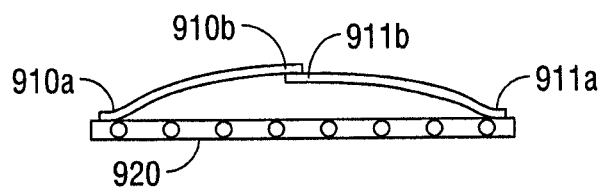

In another embodiment, shown in FIG. 9, an implantable device 900 may include a first mesh portion 920a attached to first film 910 and second mesh portion 920b attached to second film 911, wherein first and second films 910 and 911 are reversibly attached. First and second films 910 and 911 each include a first outer edge 910a and second outer edge 911a and a first inner edge 910b and second inner edge 911b, wherein the second inner edge overlaps the first inner edge. The inner perimeter portions of the first and second films may be reversibly attached via a connector, such as an adhesive, suture, clip and/or barbs. For instance, an adhesive or clip may be positioned along the inner perimeter of at least one of the first and second films to removably attach the two films together. It is envisioned that such films may be peeled apart to create an opening for the passage of tissue and then reattached with the tissue positioned within the aperture of the implant between the film and the mesh.

Although shown previously as generally square and/or rectangular in shape, the implants described herein including the film, and the mesh may be of any shape and in any combination of shapes.

The implants described herein may be useful in many endoscopic, laparoscopic, arthroscopic, endoluminal, transluminal, and/or open surgical procedures. Some examples include hernia repair, repair of vaginal prolapse, ligament repair, tendon repair, and the like. Although the polymeric films described herein may be made from ay biocompatible materials, in certain procedures, the film layers may be made from anti-adhesive materials. For example, when implanting the medical devices described herein into tissue near Cooper's ligament, it might be useful to have the flexibility to wrap around or surround the ligament, or any other sensitive tissue such as the spermatic cord, tendons, intestinal tissue, etc.

It will be understood that various modifications may be made to the embodiments disclosed herein. For example, in embodiments the medical device may rolled prior to being delivered into the body via a cannula, trocar or laparoscopic delivery device. In another example, the medical devices described herein may be sterilized and packaged into using any suitable sterilization process, i.e., gamma radiation, and any suitable medical device package, i.e., a foil pouch, peelable container, Tyvek® package, and/or an injectable medical device package. In still other examples, the implants described herein may include more than one film, and/or mesh along any surface of the mesh and/or film. Thus, those skilled in the art will envision other modifications within the scope and spirit of the claims.

What is claimed is:

1. An implantable medical device comprising:
   a first mesh having a first outer edge and a first inner edge,
   a second mesh having a second outer edge and a second inner edge, wherein the first and second inner edges are removably affixed to each other and positioned between the first and second outer edges, and
   a film having at least a first portion attached to the first outer edge of the first mesh and at least a second portion attached to the second outer edge of the second mesh.

2. The implantable medical device of claim 1 wherein at least one of the film, the first mesh and the second mesh further comprises at least one therapeutic agent.

3. The implantable medical device of claim 2 wherein the at least one therapeutic agent comprises a drug selected from the group consisting of lidocaine, bupivacaine, capsaicin, tetracaine, procaine, dibucaine, sirolimus, taxol, chlorhexidine, polyhexamethylene, thiamylal sodium, thiopental sodium, ketamine, flurazepam, amobarbital sodium, phenobarbital, bromovalerylurea, chloral hydrate, phenyloin, ethotoin, trimethadione, primidone, ethosuximide, carbamazepine, valproate, acetaminophen, phenacetin, aspirin, sodium salicylate, aminopyrine, antipyrine, sulpyrine, mepirizole, tiaramide, perixazole, diclofenac, anfenac, buprenorphine, butorphanol, eptazocine, dimenhydrinate, difenidol, dl-isoprenaline, chlorpromazine, levomepromazine, thioridazine, fluphenazine, thiothixene, flupenthixol, floropipamide, moperone, carpipramine, clocapramine, imipramine, desipramine, maprotiline, chlordiazepoxide, clorazepate, meprobamate, hydroxyzine, saflazine, ethyl aminobenzoate, chlorphenesin carbamate, methocarbamol, acetylcholine, neostigmine, atropine, scopolamine, papaverine, biperiden, trihexyphenidyl, amantadine, piroheptine, profenamine, levodopa, mazaticol, diphenhydramine, carbinoxamine, chlorpheniramine, clemastine, aminophylline, choline, theophylline, caffeine, sodium benzoate, isoproterenol, dopamine, dobutamine, propranolol, alprenolol, bupranolol, timolol, metoprolol, procainamide, quinidine, ajmaline, verapamil, aprindine, hydrochlorothiazide, acetazolamide, isosorbide, ethacrynic acid, captopril, enalapril, delapril, alacepril, hydralazine, hexamethonium, clonidine, bunitrolol, guanethidine, bethanidine, phenylephrine, methoxamine, diltiazem, nicorandil, nicametate, nicotinic-alcohol tartrate, tolazoline, nicardipine, ifenprodil, piperidinocarbamate, cinepazide, thiapride, dimorpholamine, levallorphan, naloxone, hydrocortisone, dexamethasone, prednisolone, norethisterone, clomiphene, tetracycline, methyl salicylate, isothipendyl, crotamiton, salicylic acid, nystatin, econazole, cloconazole, vitamin $B_1$, cyclothiamine, vitamin $B_2$, vitamin $B_3$, vitamin $B_5$, vitamin $B_6$, vitamin $B_7$, vitamin $B_9$, vitamin $B_{12}$, vitamin C, nicotinic acid, folic acid, nicotinamide, calcium pantothenate, pantothenol, panthetin, biotin, ascorbic acid, tranexamic acid, ethamsylate, protamine, colchicine, allopurinol, tolazamide, glymidine, glybuzole, metoformin, buformin, orotic acid, azathioprine, lactulose, nitrogen mustard, cyclophophamide, thio-TEPA, nimustine, thioinosine, fluorouracil, tegafur, vinblastine, vincristine, vindesine, mitomycin C, daunorubicin, aclarubicin, procarbazine, cisplatin, methotrexate, benzylpenicillin, amoxicillin, penicillin, oxycillin, methicillin, carbenicillin, ampicillin, cefalexin, cefazolin, erythromycin, kitasamycin, chloramphenicol, thiamphenicol, minocycline, lincomycin, clindamycin, streptomycin, kanamycin, fradiomycin, gentamycin, spectinomycin, neomycin, vanomycin, tetracycline, ciprofloxacin, sulfanilic acid, cycloserine, sulfisomidine, isoniazid, ethambutol, acyclovir, gancyclovir, vidabarine, azidothymidine, dideoxyinosine, dideoxycytosine, morphine, codeine, oxycodone, hydrocodone, cocaine, pethidine, fentanyl, polymeric forms of any of the above drugs and any combinations thereof.

4. The implantable medical device of claim 2 wherein the at least one therapeutic agent is selected from the group consisting of bupivacaine and bupivacaine hydrochloride.

5. The implantable medical device of claim 1 further comprising at least one connector positioned on at least one of the first and second mesh.

6. The implantable medical device of claim 5 wherein the at least one connector comprises a grip-member.

7. The implantable medical device of claim 1 wherein the at least one connector comprises a barb.

8. The implantable medical device of claim 1 wherein the at least one connector comprises an adhesive.

9. The implantable medical device of claim 1, wherein the film comprises a biodegradable material.

10. The implantable medical device of claim 1 wherein the film comprises a copolymer of glycolide and caprolactone.

11. The implantable medical device of claim 1 wherein the film comprises a copolymer of glycolide, trimethylene carbonate, caprolactone and lactide.

12. The implantable medical device of claim 1 wherein the film comprises a copolymer of glycolide, dioxanone, and trimethylene carbonate.

13. The implantable medical device of claim 1, wherein the film comprises an aliphatic polyester.

14. The implantable medical device of claim 1, wherein the film comprises collagen.

15. The implantable medical device of claim 1, wherein at least one of the first and second mesh comprise a non-bioabsorbable material.

16. The implantable medical device of claim 1, wherein at least one of the first and second mesh comprise a non-bioabsorbable polyester.

17. The implantable medical device of claim 16, wherein at least one of the first and second mesh comprise polypropylene.

18. The implantable medical device of claim 1, wherein at least one of the first and second mesh comprise an animal-derived tissue.

19. The implantable medical device of claim 1, wherein at least one of the first and second mesh comprise an allograft or a xenograft.

20. An implantable medical device comprising:
a film having at least a first portion, a second portion, and body portion positioned therebetween,
a first mesh having a first outer edge attached to the first portion of the film and a first inner edge unattached to the film,
a second mesh having a second outer edge attached to the second portion of the film and a second inner edge unattached to the film, wherein the first and second inner edges of the first and second mesh are removably affixed to each other.

* * * * *